United States Patent [19]

DeLuca et al.

[11] Patent Number: 4,689,180

[45] Date of Patent: Aug. 25, 1987

[54] 1α,25-DIHYDROXY-22Z-DEHYDROXYVITAMIN D COMPOUND

[75] Inventors: Hector F. DeLuca; Heinrich K. Schnoes; Rafal R. Sicinski; Yoko Tanaka, all of Madison, Wis.

[73] Assignee: Wisconsin Alumni Research Foundation, Madison, Wis.

[21] Appl. No.: 794,324

[22] Filed: Nov. 4, 1985

Related U.S. Application Data

[63] Continuation of Ser. No. 575,114, Jan. 30, 1984, abandoned.

[51] Int. Cl.$^4$ ............................................. C07J 9/00
[52] U.S. Cl. ................................................. 260/397.2
[58] Field of Search ..................................... 260/397.2

[56] References Cited

U.S. PATENT DOCUMENTS 4,260,549  4/1981  DeLuca et al. ............... 260/397.2

Primary Examiner—Leonard Schenkman
Assistant Examiner—Joseph A. Lipovsky
Attorney, Agent, or Firm—Howard W. Bremer

[57] ABSTRACT

The invention provides a novel vitamin D derivative, 1α,25-dihydroxy-22Z-dehydrovitamin $D_2$.

The compound is characterized by unexpectedly high ability to raise serum calcium levels. The compound could therefore, find ready application as a substitute for vitamin D or its metabolites in the treatment of metabolic bone diseases or in other of their known applications.

2 Claims, No Drawings

1α,25-DIHYDROXY-22Z-DEHYDROXYVITAMIN D COMPOUND

DESCRIPTION

This invention was made with Government support under NIH Grant No. AM 14881 awarded by the Department of Health and Human Services. The Government has certain rights in this invention.

This application is a continuation of application Ser. No. 575,114, filed Jan. 30, 1984, now abandoned.

TECHNICAL FIELD

This invention relates to a biologically active vitamin D compound. Specifically, the invention relates to a novel 1α,25-dihydroxylated vitamin D compound with a 22,23-cis-double bond in the side chain, and to a method for its preparation.

BACKGROUND

Calcium and phosphate homeostasis in animals and humans is regulated by vitamin D metabolites, and the compound 1α,25-dihydroxyvitamin $D_3$ is generally considered as the most active and most important vitamin D-derived regulator of normal calcium and phosphate balance. This natural metabolite and compounds structurally related to it are therefore of great pharmaceutical interest as effective agents for the prevention and treatment of bone diseases and related calcium metabolism disorders. In addition to the natural $D_3$ metabolites, a number of compounds have been prepared in recent years which, because of their high potency, find use or show very considerable promise as therapeutic agents, among them 1α-hydroxyvitamin $D_3$, 1α-hydroxyvitamin $D_2$, 1α,25-dihydroxyvitamin $D_2$ and certain fluorinated analogs (U.S. Pat. Nos. 3,741,996; 3,907,843; 3,880,894; 4,226,788; 4,358,406). Most of the known active analogs are characterized by the type of sterol side chain as it occurs in vitamin $D_3$ (i.e. saturated side chain). Known analogs with 22,23-unsaturated side chain are represented by compounds of the vitamin $D_2$ series (i.e. 22,23-trans-unsaturated with a C-24-methyl substituent), and include, in addition to the compounds named above, 25-hydroxyvitamin $D_2$ (U.S. Pat. No. 3,585,221) and the 24- and 24,25-dihydroxy derivatives (Jones et al. Arch. Biochem. Biophys. 202, 450 (1980)) and three compounds lacking the 24-methyl substituent (U.S. Pat. No. 3,786,062; Bogoslovskii et al. J. Gen. Chem. USSR, 48(4) 828 (1978); Chem. Abstr. 89, 163848j, 209016s).

DISCLOSURE OF INVENTION

A novel vitamin D analog has now been found which may be represented by structure I shown below:

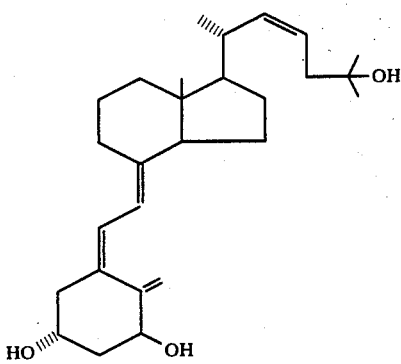

This novel compound is characterized by a 22,23-double bond in the side chain having the cis (or Z) geometry. Because of the presence of this 22Z-double bond, which results in a quite different side chain geometry from that pertaining to compounds having the normal saturated side chain (e.g. as in 1α,25-dihydroxyvitamin $D_3$) or a 22,23-trans (22E)-unsaturated side chain (e.g. as in 1α,25-dihydroxyvitamin $D_2$), it was assumed that this cis-unsaturated product would exhibit low biological activity, if any. Surprisingly, this material, in spite of its altered side chain structure, shows high activity, being as active as 1α,25-dihydroxyvitamin $D_3$ in its ability to raise serum calcium levels in test animals.

PREPARATION OF THE COMPOUND

The novel product of this invention, compound I, above, was prepared from a 22Z-dehydrovitamin D precursor having the structure II shown below, by in vitro enzymatic hydroxylation at carbon 25 using a liver homogenate preparation from vitamin D-deficient rats.

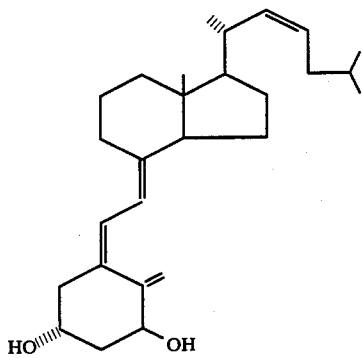

The following procedure was used: Male weanling rats were fed a low calcium and vitamin D-deficient diet as described by Suda et al. [J. Nutr. 100, 1049 (1970)] for 2 weeks. They were killed by decapitation and their livers were removed. A 20% (w/v) homogenate was prepared in ice-cold 0.25 M sucrose. Incubation was carried out in 10 ml incubation medium in a 125 ml Erlenmayer flask containing an aliquot of liver homogenate representing 1 g of tissue, 0.125M sucrose, 50 mM phosphate buffer (pH 7.4), 22.4 mM glucose-6-phosphate, 20 m ATP, 160 mM nicotinamide, 25 mM succinate, 0.4 mM NADP, 5 mM $MgCl_2$, 0.1M KCl and 0.5 units glucose-6-phosphatedehydrogenase. The reaction was initiated by addition of 400 μg of the substrate, compound II above, dissolved in 100 μl 95% ethanol. The incubation mixture was incubated at 37° C. with shaking at 80 oscillations/min for 3 h. The reaction was stopped by addition of 20 ml methanol and 10 ml dichloromethane. After further addition of 10 ml dichloromethane, the organic phase was collected while the aqueous phase was re-extracted with 10 ml dichloromethane. The organic phases from total of three extractions were combined and evaporated with a rotary evaporator. The residue containing the desired product was dissolved in 1 ml of CHCl$_3$:hexane (65:35) mixture and applied to a Sephadex LH-20 column (0.7 cm × 14 cm) packed, equilibrated and eluted with the same solvent. The first 10 ml was discarded while next 40 ml was collected and evaporated. The residue was then dissolved in 8% 2-propanol in hexane and subjected to high performance liquid chromatography (Model LC/GPC 204 HPLC, Waters Associates, Medford, MA) using a Zorbax-SIL column (4.6 mm × 25 cm, Dupont, Wilmington, Del.) operating under pressure of 1000 psi with a flow rate of 2 ml/min. The desired 25-hydroxylated product was eluted at 44 ml. This product was further purified by high performance liquid chromatography using a reversed phase column (Richrosorb Rp-18, 4.6 mm × 25 cm, E. Merck, Darmstadt, West Germany) operated under pressure of 1200 psi and a flow rate of 2 ml/min. The column was eluted with 22% H$_2$O in methanol, and the compound was eluted at 50 ml. The product was further purified by HPLC using the Zorbax-SIL column and conditions as described above. The resulting product was then subjected to physical characterization.

CHARACTERIZATION OF THE PRODUCT

The UV absorption of the product in 95% ethanol exhibited a $\lambda_{max}=265$ nm and a $\lambda_{min}=228$ nm indicating the presence of the 5,6-cis-triene chromophore.

The mass spectrum of the substance contains a molecular ion at m/e 414 as required for a 25-hydroxylated product. Elimination of one and two molecules of H$_2$O gives fragment ions at m/e 396 and 378. Loss of the entire steroid side chain (cleavage of C$_{17}$/C$_{20}$ bond) results in the fragment of m/e 287, which by elimination of one and two molecules of H$_2$O, gives rise to the peaks at m/e 269 and 251. The spectrum shows prominent peaks at m/e 152 and 234 (152-H$_2$O) which represent ring A fragments and are diagnostic for 1α,3β-dihydroxyvitamin D compounds. In addition, the spectrum shows a very prominent fragment peak at m/e 59 which results from cleavage of the C$_{24}$/C$_{25}$ bond. The presence of this ion confirmed the presence of 25-hydroxy group in the product. Thus, these data established the structure of the product obtained as the 1α,25-dihydroxylated compound, as represented by structure I, above.

BIOLOGICAL ACTIVITY

The biological activities of the novel analog was demonstrated by in vivo assay in the rat. Male weanling rats were fed the low calcium vitamin D-deficient diet of Suda et al. (supra) for 3 weeks. They were then divided into groups of 5 rats each. Rats in a control group received 0.05 ml 95% ethanol intrajugularly while rats in the other groups were given 325 pmole of either compound I or 1α,25-dihydroxyvitamin D$_3$ dissolved in 0.05 ml 95% ethanol. Eighteen hours later, they were killed by decapitation and blood was collected. Serum obtained by centrifugation of the blood was diluted with 0.1% lanthanum chloride solution (1:20) and serum calcium concentration was determined with an atomic absorption spectrophotometer. Results are shown in the following Table:

| Increase in serum calcium concentration in response to a single dose of 325 pmole of either compound I or 1α,25-dihydroxyvitamin D$_3$ given 18 h prior to sacrifice | |
|---|---|
| Compound Given | Serum Calcium Concentration (mg/100 ml) ± standard deviation |
| ethanol | 4.2 ± 0.1[a] |
| compound I | 5.2 ± 0.2[b] |
| 1α,25-dihydroxyvitamin D$_3$ | 5.4 ± 0.4[b] |

[b]is significantly different from
[a]p < 0.001

The above results show the new analog to be highly potent and to exhibit biological activity essentially equivalent to that of 1α,25-dihydroxyvitamin D$_3$.

Because of this high potency, the compound of this invention will find application as a therapeutic agent in the therapy or prophylaxis of disorders such as the various types of rickets, hypoparathyroidism, osteodystrophy, osteomalacia or osteoporosis in the human, or for the treatment of related calcium deficiency diseases (e.g. milk fever, leg weakness, egg shell thinness) in animals. Likewise the compound may be used for the treatment of certain malignancies, such as human leukemia.

For therapeutic purposes, the compound may be administered by any conventional route of administration and in any form suitable for the method of administration selected. The compound may be formulated with any acceptable and innocuous pharmaceutical carrier, in the form of pills, tablets, gelatin capsules, or suppositories, or as solutions, emulsions, dispersions or suspensions in innocuous solvents or oils, and such formulations may contain also other therapeutically active and beneficial ingredients as may be appropriate for the specific applications. For human applications, the compound is advantageously administered in amounts from 0.25 to 10 μg per day, the specific dosage being adjusted in accordance with the disease to be treated and the medical history, condition and response of the subject, as is well understood by those skilled in the art.

The 22Z-dehydro precursor substrate, compound II above, required for the preparation of the novel product of this invention is itself prepared by the process depicted in Process Scheme I, appended, and described below. In the description, compound designation by Arabic numerals (e.g. (b 1), (2), (3), etc.) refer to the structures so numbered in the Process Scheme. The desired substrate (compound II) for the above described 25-hydroxylation reaction is identified by Arabic numeral (11) in Process Scheme I and in the following description.

(22Z)-3β-(Methoxymethoxy)-5α,8α-(4-phenyl-1,2-urazolo)cholesta-6,22-dien (2).

Isopentyl phosphonium bromide [(CH$_3$)$_2$CHCH$_2$CH$_2$PPh$_3$Br] (1.67 g, 4.04 mmol) in dry tetrahydrofuran (73 ml) was treated with n-butyllithium (1.7M solution in hexane, 2.42 ml, 4.11 mmol) at 3°–5° C. with stirring. After stirring for 1 h at room temperature, the orange-red solution was cooled to 3° C. and aldehyde (1) (1.84 g, 3.36 mmol) in dry THF (24 ml) was added. The colorless reaction mixture was stirred overnight at room temperature and then poured into water and extracted with benzene. The organic extract was washed with 5% HCl, saturated sodium bicarbonate and water, dried (Na$_2$SO$_4$) and concentrated in a vacuo to an oil, which was purified on a column of silica gel. Elution with benzene-ether (94:6) mixture afforded adduct (2) (1.38 g, 68%) as a foam: NMR δ 0.83 (3H, s, 18-H$_3$), 0.89 and 0.91 (6H, each d, J=6.8 Hz, 26-H$_3$ and 27-H$_3$), 0.97 (3H, d, J=6.8 Hz, 21-H$_3$), 0.98 (3H, s, 19-H$_3$), 3.30 (1H, dd, J$_1$=4.4 Hz, J$_2$=14 Hz, 9-H), 3.38 (3H, s, OCH$_3$), 4.33 (1H, m, 3-H), 4.70 and 4.81 (2H, ABq, J=6.8 Hz, OCH$_2$O), 5.21 (2H, br m, 22-H and 23-H), 6.23 and 6.39 (2H, ABq, J=8.5 Hz, 6-H and 7-H), 7.41 (5H, br m, Ar-H); IR: 1756, 1703, 1601, 1397, 1046 cm$^{-1}$; mass spectrum, m/z 601 (M$^+$, 1%), 426 (4), 364 (61), 349 (16), 253 (18), 251 (18), 119 (PhNCO, 100).

(22Z)-5α,8α-(4-phenyl-1,2-urazolo)cholesta-6,22-dien-3β-ol (3).

A solution of adduct (2) (601 mg, 1 mmol) and p-toluenesulfonic acid (523 mg, 2.75 mmol) in methanol (20 ml)-THF (12 ml) mixture was stirred for 2 days at room temperature. The reaction mixture was poured into saturated sodium bicarbonate and extracted several times with benzene. Extracts were washed with water, dried (Na$_2$SO$_4$) and evaporated under reduced pressure. Purification of the crude product by column chromatography (benzene ether 70:30 as eluant) gave the hydroxy adduct (3) (550 mg, 99%) as a foam: NMR δ 0.83 (3H, s, 18-H$_3$), 0.89 and 0.91 (6H, each d, J=6.8 Hz, 26-H$_3$ and 27-H$_3$), 0.95 (3H, s, 19-H$_3$), 0.98 (3H, d, J=6.8 Hz, 21-H$_3$), 3.16 (1H, dd, J$_1$=4.4 Hz, J$_2$=14 Hz, 9-H), 4.44 (1H, m, 3-H), 5.22 (2H, br m, 22-H and 23-H), 6.22 and 6.39 (2H, ABq, J=8.5 Hz, 6-H and 7-H), 7.40 (5H, br m, Ar-H); IR: 3447, 1754, 1700, 1600, 1397 cm$^{-1}$; mass spectrum, m/z (557 (M$^+$, 1%) 382 (35), 349 (33), 253 (20), 251 (33), 119 (100), 55 (82).

(22Z)-Cholesta-5,7,22-trien-3β-ol (4)

The adduct (3) (530 mg, 0.95 mmol) was converted to the diene (4) by reduction with lithium aluminum hydride (1 g), in tetrahydrofuran (60 ml) at reflux for 18 h. After conventional work-up, the product was purified by chromatography over silica (benzene-ether 94:6 as eluant) to afford pure diene (4) (290 mg, 76%) after crystallization from ethanol:mp 148°-151° C.; [α]$_D^{24}$=−132° (c=0.9, CHCl$_3$); NMR δ 0.66 (3H, s, 18-H$_3$), 0.90 and 0.91 (6H, each d, J=6.8 Hz, 26-H$_3$ and 27-H$_3$), 0.96 (3H, s, 19-H$_3$), 0.98 (3H, d, J=6.9 Hz, 21-H$_3$), 3.64 (1H, m, 3-H), 5.20 (2H, br m, 22-H and 23-H), 5.39 and 5.57 (2H, ABq, J=6 Hz, 7-H and 6-H); UV λ$_{max}$ 281 nm; IR: 3346, 1463, 1375, 1364, 1067, 1040, 831 cm$^{-1}$; mass spectrum, m/z 382 (M$^+$, 100), 349 (65); 323 (32), 271 (15), 253 (30).

(5Z,7E,22Z)-9,10-Secocholesta-5,7,10(19),22-tetraen-3β-ol (5).

Irradiation of 5,7-diene (4) (150 mg, 0.39 mmol) dissolved in ether (120 ml) and benzene (30 ml) (degassed with argon for 40 min) was performed at 0° C. for 13 min using a UV-lamp and Vycor filter. HPLC (1% of 2-propanol in hexane) of the resulting mixture afforded the previtamin (56.9 mg, 38%) as a colorless oil: NMR δ0.75 (3H, s, 18-CH$_3$), 0.90 and 0.91 (6H, each d, J=6.7 Hz, 26-H$_3$ and 27-H$_3$), 0.99 (3H, d, J=6.8 Hz, 21-H$_3$), 1.64 (3H, s, 19-H$_3$), 3.90 (1H, m, 3-H), 5.20 (2H, br m, 22-H and 23-H), 5.69 and 5.95 (2H, ABq, J=12 Hz, 7-H and 6-H); UV λ$_{max}$ 261 nm, λ$_{min}$ 234 nm.

Thermal isomerization of this previtamin intermediate (56 mg, 0.15 mmol) in refluxing ethanol (3 h) gave the oily vitamin analog (5) (43 mg, 77%) after separation by HPLC. NMR δ 0.60 (3H, s, 18-H$_3$), 0.89 and 0.90 (6H, each d, J=6.7 Hz, 26-H$_3$ and 27-H$_3$), 0.97 (3H, d, J=6.6 Hz, 21-H$_3$), 3.96 (1H, s, 3-H), 4.82 and 5.05 (2H, each narr. m, 19-H$_2$), 5.20 (2H, br m, 22-H and 23-H), 6.04 and 6.24 (2H, ABq, J=11.4 Hz, 7-H and 6-H); UV λ$_{max}$ 265.5 nm, λ$_{min}$ 228 nm; IR: 3427, 1458, 1379, 1048, 966, 943, 892 cm$^{-1}$; mass spectrum, m/z 382 (M$^+$, 21), 349 (5), 271 (8), 253 (14), 136 (100), 118 (82). Vitamin analog (5) is a known compound (Bogoslovskii et al., supra).

1-Hydroxylation of compound (5).

Freshly recrystallized p-toluenesulfonyl chloride (50 mg, 0.26 mmol) was added to a solution of vitamin (5) (50 mg, 0.13 mmol) in dry pyridine (300 μl). After 30 h at 4° C., the reaction mixture was poured into ice/saturated NaHCO$_3$ with stirring. The mixture was stirred for 15 min and extracted with benzene. The organic extract was washed with saturated NaHCO$_3$, saturated copper sulfate and water, dried (Na$_2$SO$_4$) and concentrated in vacuo to obtain the oily tosylate (6). The crude tosylate (6) was treated with NaHCO$_3$ (150 mg) in anhydrous methanol (10 ml) and the mixture was stirred for 8.5 h at 55° C. After cooling and concentration to 2 ml the mixture was diluted with benzene (80 ml), washed with water, dried (Na$_2$SO$_4$) and evaporated under reduced pressure. The oily 3,5-cyclovitamin D compound (7) thus obtained was sufficiently pure to be used for the following oxidation step without any purification. To a vigorously stirred suspension of SeO$_2$ (5.1 mg, 0.046 mmol) in dry CH$_2$Cl$_2$ (5 ml), tert-butylhydroperoxide (16.5 μl, 0.118 mmol) was added. After 30 min dry pyridine (50 μl) was added and the mixture was stirred for additional 25 min at room temperature, diluted with CH$_2$Cl$_2$ (3 ml) and cooled to 0° C. The crude 3,5-cyclovitamin product (7) in CH$_2$Cl$_2$ (4.5 ml) was then added. The reaction proceeded at 0° C. for 15 min and then it was allowed to warm slowly (30 min) to room temperature. The mixture was transferred to a separatory funnel and shaken with 30 ml of 10% NaOH. Ether (150 ml) was added and the separate organic phase was washed with 10% NaOH, water and dried over Na$_2$SO$_4$. Concentration to dryness in vacuo gave a yellow oily residue which was purified on silica gel TLC plate developed in 7:3 hexane-ethyl acetate giving 1-hydroxycyclovitamin product (20 mg, 37%): NMR δ 0.59 (3H, s, 18-H$_3$), 0.63 (1H, m, 3-H), 0.89 and 0.90 (6H, each d, J=6.9 Hz, 26-H$_3$ and 27-H$_3$), 0.96 (3H, d, J=6.9 Hz, 21-H$_3$), 3.25 (3H, s, —OCH$_3$), 4.17 (2H, m, 1-H and 6-H), 4.96 (1H, d, J=9.3 Hz, 7-H), 5.1–5.4 (4H, br m, 19-H$_2$, 22-H nd 23-H); mass spectrum, m/z 412 (M$^+$, 26), 380 (48), 339 (22), 269 (28), 245 (20), 135 (100). This product is composed chiefly of the 1α-hydroxycyclovitamin D compound of structure (8), as well as small amount of the corresponding 1β-hydroxy-epimer. These components may be separated at this stage, if desired, but such separation is not required.

The 1-hydroxycyclovitamin product (18 mg) as obtained above was heated (55° C./15 min) in glacial acetic acid (0.8 ml), the mixture was neutralized (ice/saturated NaHCO$_3$) and extracted with benzene and ether, to yield after HPLC (1.5% of 2-propanol in hexane as eluent) separation pure 1α-hydroxy-3β-acetoxyvitamins (9) (6.60 mg, 34%, eluting at 42 ml) and (10) (4.20 mg, 22%, eluting at 50 ml). Compound (9): NMR δ 0.60 (3H, s, 18-H$_3$), 0.90 and 0.92 (6H, each d, J=7.0 Hz, 26-H$_3$ and 27-H$_3$), 0.97 (3H, d, J=6.8 Hz, 21-H$_3$), 2.04 (3H, s, —OCOCH$_3$), 4.41 (1H, m, 1-H), 5.02 (1H, narr. m, 19-H), 5.1–5.4 (4H, br m, 3-, 19-, 22- and 23-H), 6.03 and 6.35 (2H, ABq, J=11.4 Hz, 7-H and 6-H); UV $\lambda_{max}$ 264.5 nm, $\lambda_{min}$ 227.5 nm; mass spectrum, m/z 440 (M+, 10), 380 (72), 362 (7), 269 (31), 251 (12), 135 (100), 134 (99). Compound (10): NMR δ 0.60 (3H, s, 18-$H_3$), 0.90 and 0.91 (6H, each d, J=7.0 Hz, 26-$H_3$ and 27-$H_3$), 0.97 (3H, d, J=6.9 Hz, 21-$H_3$), 2.05 (3H, s, —O—COC$H_3$), 4.49 (1H, m, 1-H), 5.00 and 5.14 (2H, each narr. m, 19-$H_2$), 5.20 (3H, br m, 3-, 22- and 23-H), 5.82 and 6.59 (2H, ABq, J=12.0 Hz, 7-H and 6-H); UV $\lambda_{max}$ 270 nm; $\lambda_{min}$ 228 nm; mass spectrum, m/z 440 (M+, 4), 380 (30), 269 (10), 135 (100), 134 (52).

Hydrolysis of 3β-acetoxy group in compounds (9) and (10).

Each of the 3β-acetoxy-derivatives (9) or (10) was separately hydrolyzed, using the same procedure. A solution of 3β-acetoxyvitamin (0.7–6 mg) in ethanol (0.1 ml) was treated with 10% KOH in methanol (0.8 ml) and the mixture was heated for 1 h at 50° C. After usual work-up and final HPLC purification (8% of 2-propanol in hexane as eluent) the corresponding 1-hydroxyvitamins were obtained, namely: Compound (11): NMR 67 0.59 (3H, s, 18-$H_3$), 0.89 and 0.90 (6H, each d, J=7.0 Hz, 26-$H_3$ and 27-$H_3$), 0.96 (3H, d, J=6.8 Hz, 21-$H_3$), 4.23 (1H, m, 3-H), 4.43 (1H, m, 1-H), 5.00 (1H, narr. m, 19-H), 5.1–5.4 (3H, br m, 19-, 22-, and 23-H), 6.02 and 6.39 (2H, ABq, J=11.4 Hz, 7-H and 6-H); UV $\lambda_{max}$ 264.5 nm, $\lambda_{min}$ 227.5 nm; mass spectrum, m/z 398 (M+, 21), 380 (8), 287 (6), 269 (7), 251 (5), 152 (36), 134 (100). (Elution volume 39 ml). Compound (12): NMR δ 0.61 (3H, s, 18-$H_3$), 0.89 and 0.91 (6H, each d, J=7.0 Hz, 26-$H_3$ and 27-$H_3$), 0.97 (3H, d, J=6.9 Hz, 21-$H_3$), 4.25 (1H, m, 3-H), 4.51 (1H, m, 1-H), 4.98 and 5.13 (2H, each narr. m., 19-$H_2$), 5.21 (2H, br m, 22-H and 23-H), 5.89 and 6.59 (2H, ABq, J=11.5 Hz, 7-H and 6-H); UV $\lambda_{max}$ 273 nm, $\lambda_{min}$ 229.5 nm; mass spectrum, m/z 398 (M+, 17), 380 (4), 287 (5), 269 (5), 251 (4), 152 (29), 134 (100). (Elution volume 38 ml).

In the above described process, high pressure liquid chromatography (HPLC) was performed on a Waters Associates Model ALC/GPC 204 using a Zorbax-Sil (DuPont) (6.2 mm×25 cm column, flow rate 4 ml/min, 1500 psi). Column chromatography was performed on Silica Gel 60, 70-230 mesh ASTM (Merck). Preparative thin-layer chromatography (TLC) was carried out on Silica 60 PF-254 (20×20 cm plates, 1 mm silica gel). Irradiations were carried out using a Hanovia 608A36 mercury arc lamp fitted with a Vycor filter. All reactions are preferably performed under an inert atmosphere (e.g. argon).

The compound of this invention can, if desired, be readily obtained in crystalline form by crystallization from suitable solvents such as hexane, ethers and alcohols (absolute or aqueous), and mixtures thereof as will be evident and well known to those skilled in the art.

Process Scheme I

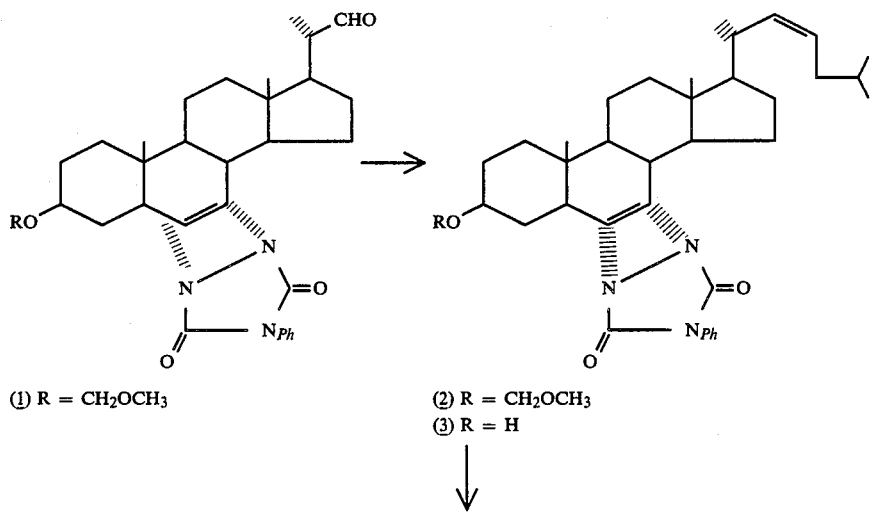

(1) R = $CH_2OCH_3$ (2) R = $CH_2OCH_3$
(3) R = H

-continued
Process Scheme I
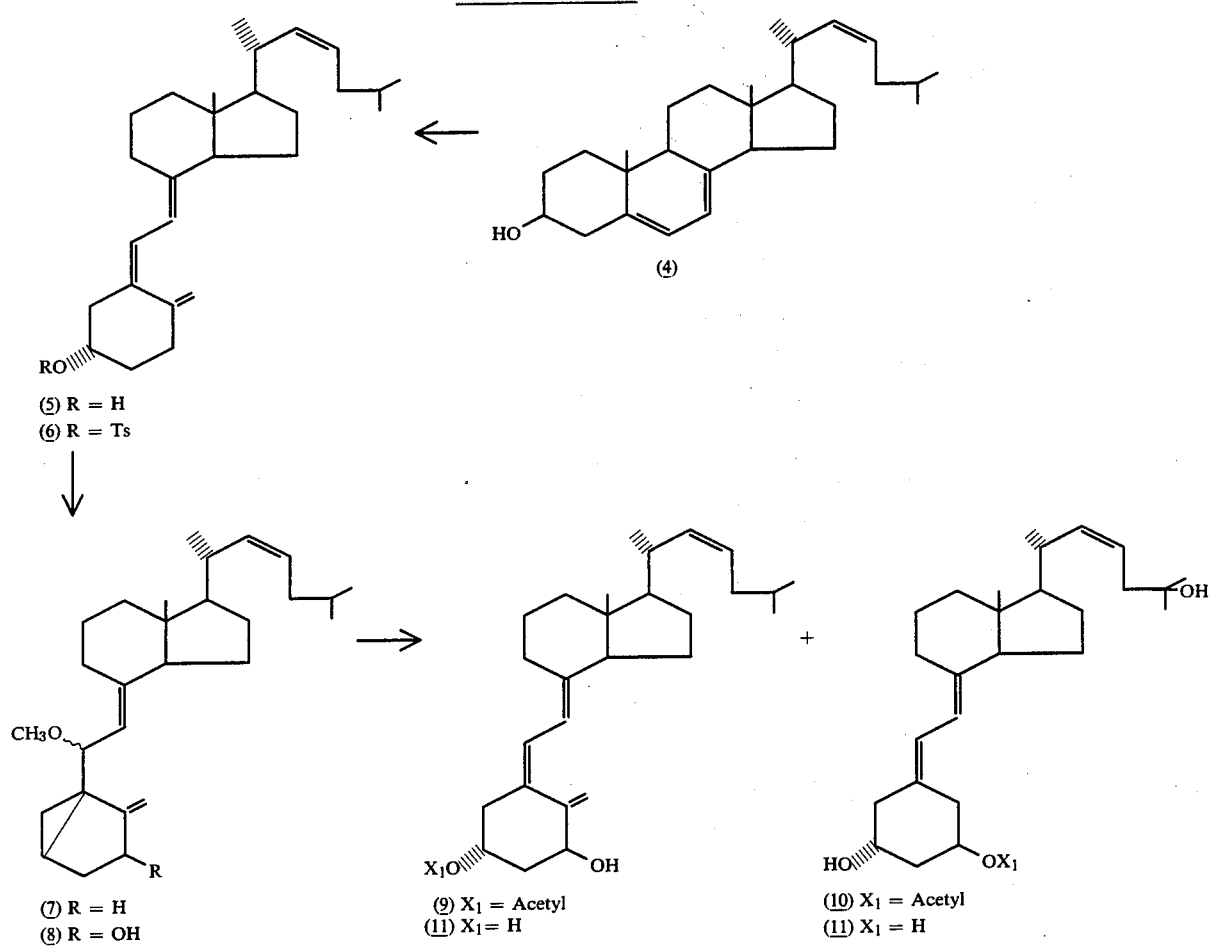
(5) R = H
(6) R = Ts
(7) R = H
(8) R = OH
(9) X₁ = Acetyl
(11) X₁ = H
(10) X₁ = Acetyl
(11) X₁ = H
We claim:
1. The compound having the structure
2. A serum calcium level raising pharmaceutical composition comprising the compound of claim 1 together with a pharmaceutically acceptable excipient.
* * * * *